United States Patent [19]

Argese et al.

[11] Patent Number: 6,162,912
[45] Date of Patent: Dec. 19, 2000

[54] PROCESS OF PREPARING TETRAACETIC ACID DERIVATIVES

[75] Inventors: Maria Argese; Giorgio Ripa, both of Milan, Italy

[73] Assignee: Dibra S.p.A., Milan, Italy

[21] Appl. No.: 09/362,186

[22] Filed: Jul. 28, 1999

Related U.S. Application Data

[62] Division of application No. 09/121,673, Jul. 23, 1998, Pat. No. 5,977,353.

[30] Foreign Application Priority Data

Jul. 25, 1997 [IT] Italy ................................ MI97A1766

[51] Int. Cl.[7] ...................... C07D 257/02; C07D 257/00
[52] U.S. Cl. .......................... 540/474; 540/450; 540/470; 540/473
[58] Field of Search ..................................... 540/474, 450, 540/470

[56] References Cited

U.S. PATENT DOCUMENTS

| | | | |
|---|---|---|---|
| 5,539,105 | 7/1996 | Uggeri et al. | 540/474 |
| 5,587,451 | 12/1996 | Athey et al. | 528/345 |
| 5,886,174 | 3/1999 | Ripa et al. | 540/474 |
| 5,977,353 | 11/1999 | Argese et al. | 540/473 |

*Primary Examiner*—Mukund J. Shah
*Assistant Examiner*—Pavanaram K Sripada
*Attorney, Agent, or Firm*—Nixon & Vanderhye

[57] ABSTRACT

The present invention relates to the novel compound, 1,4,7,10-tetraazabicyclo[8.2.2]tetradecan-2-one of formula (I), its preparation and the use thereof for the preparation of tetraazamacrocycles.

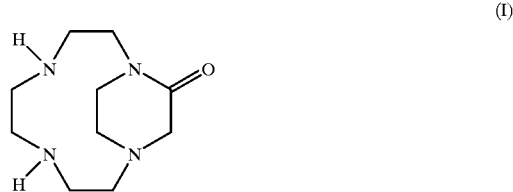

(I)

7 Claims, No Drawings

PROCESS OF PREPARING TETRAACETIC ACID DERIVATIVES

This application is a division of Ser. No. 09/121,673, filed Jul. 23, 1998, U.S. Pat. No. 5,977,353.

The present invention relates to the novel compound, 1,4,7,10-tetraazabicyclo[8.2.2]tetradecan-2-one of formula (I), its preparation and the use thereof for the preparation of tetraazamacrocycles.

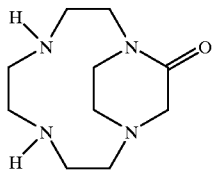
(I)

The compound of formula (I) was surprisingly synthesized starting from compound of formula (II), 2α,4α,6α,8α-decahydro-teatraazacyclopent[fg]acenaphthylene, already known as an intermediate for the preparation of polyazamacrocycles derivatives.

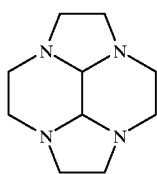
(II)

The compound of formula (II) can, in its turn, be obtained starting from straight polyamines, as described in Italian Patent application MI 96A 001257, and it can be converted to 1,4,7,10-tetraazacyclododecane (commonly named Cyclen) according to the following scheme:

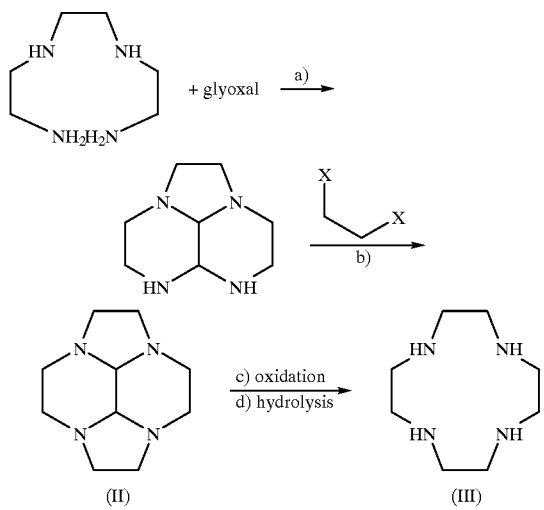

in which step a) is the condensation of triethylenetriamine with a glyoxal derivative (glyoxal hydrate, or Bertagnini's salt), in water or in water-soluble solvents or in mixtures thereof, at temperatures from 0 to 50° C., in the presence of stoichiometric amounts or in a slight excess of calcium hydroxide; step b) is the condensation of the resulting compound from step a) with an $X-CH_2-CH_2-X$ alkylating agent, in which X is a halogen or a sulfonic acid reactive derivative, in at least stoichiometric amounts, in the presence of at least two moles of a base selected from alkali or alkaline-earth metal carbonates per mole of substrate, at a temperature of 25–150° C., to give the compound of formula (II);

step c) is the oxidation of the compound of formula (II) with a suitable oxidizing agent for aliphatic amines, in water or in a diphasic system consisting of water and an organic solvent, resistant to such conditions, at temperatures from 0 to 100° C., to give a mixture of oxidized products which is subjected directly to step d), consisting of the hydrolysis, either in aqueous acidic medium at pH lower than 2, or in an aqueous basic medium at pH higher than 12, at temperatures of 110–200° C., to give the compound of formula (III).

Compound (III) is the starting material for the synthesis of polydentated derivatives capable of complexing different metals, some of which find use in the biomedical field, such as gadolinium complexes of said derivatives, which are used in the medical diagnostic field as contrast agents for the resonance technique (Magnetic Resonance Imaging, MRI).

At present, two contrast media are commercially available, namely Dotarem[R] (gadolinium complex of 1,4,7,10-tetraazacyclododecane-1,4,7,10-tetraacetic acid meglumine salt), and ProHance[R] [Gadoteridol, gadolinium complex of 10-(2-hydroxypropyl)-1,4,7,10-tetraazacyclododecane-1,4,7-triacetic acid]; on the other hand, Gadobutrol is a contrast medium at present under development (gadolinium complex of [10-[2,3-dihydroxy-1-(hydroxymethyl)propyl]-1,4,7,10-tetraazacyclododecane-1,4,7-triacetic acid])

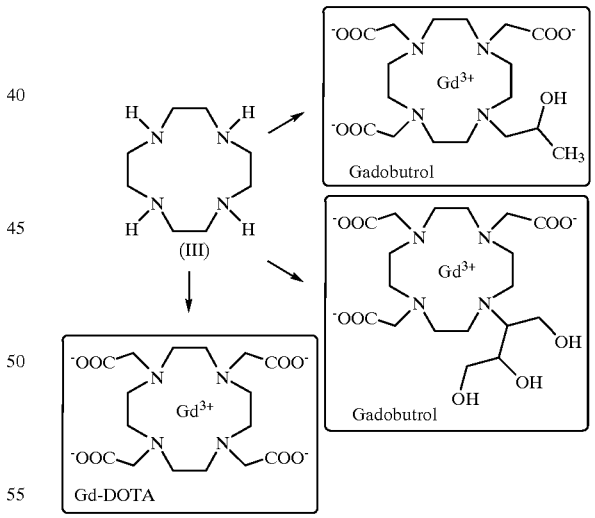

The possible procedures for the conversion of compound (II) to 1,4,7,10-tetraazacyclododecane (III) were described in WO 96/28432 and in MI 96A 001257, and they are based on suitably optimized hydrolytic or oxidizing conditions for the preparation of compound (III).

These novel synthetic routes for the preparation of compound (III) are an important improvement of the conventional synthesis by Richman-Atkins (J. Am. Chem. Soc., 1974, 96, 2268) based on the use of tosyl derivatives, in that they provide simpler, more economic and environmentally safer industrial processes.

However, except for Gd-DOTA, obtainable from 1,4,7,10-tetraazacyclododecane (III) by alkylation of the four nitrogen atoms and subsequent complexation of the intermediate 1,4,7,10-tetraazacyclododecane-1,4,7,10-tetraacetic acid, macrocycle (III) cannot, as a rule, be used directly for the preparation of gadolinium complexes wherein the macrocycle nitrogen atoms are variously substituted.

In these cases it is, in fact, necessary to make use of the selective protection of the nitrogen atoms to direct the subsequent functionalization of the macrocycle towards the desired positions.

For example, the key intermediate of the synthesis of Gadoteridol and Gadobutrol is 1,4,7,10-tetraazacyclododecane-1,4,7-triacetic acid (DO3A), preparabile starting from (III) (see for ex.: Tweedle et al., Inorg. Chem., 1265, 1991) through the tricyclic intermediate of formula (IV) according to the scheme reported in the following.

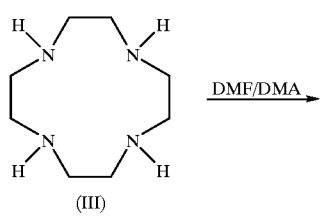

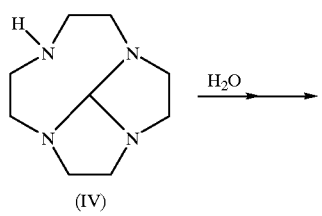

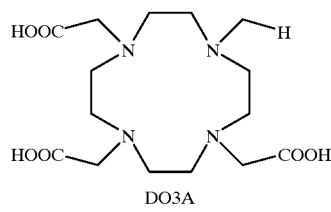

When such disubstituted derivatives of compound (III) are desired, as, for example, 1,4,7,10-tetraazacyclododecane-1,7-diacetic acid (1,7-DO2A), the synthetic route starting from macrocycle (III) is extremely complex, as described, for example, by Sherry in a paper (J. Chem. Soc. Chem. Commun., 1995, 185) and it is based on a series of selective protections, which make use of reactives rather unsuitable for possible industrial applications, mainly due to economic and environmental reasons;

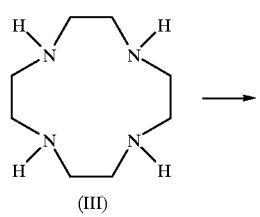

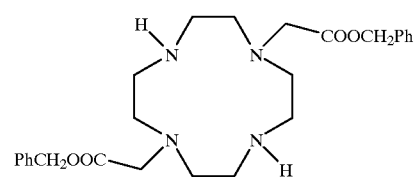

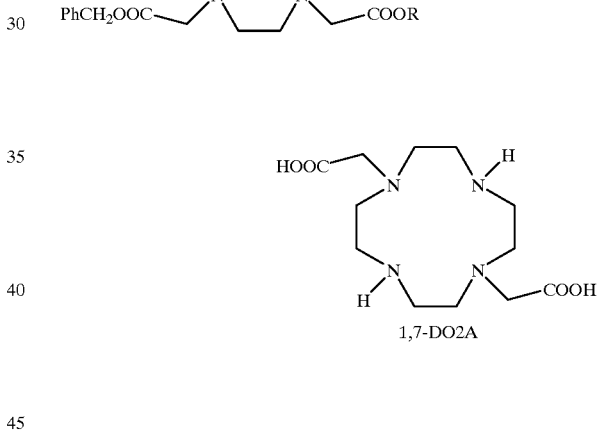

or as described by the same author in WO 93/12097, which, however, involves the use of cyanides.

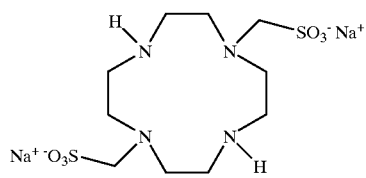

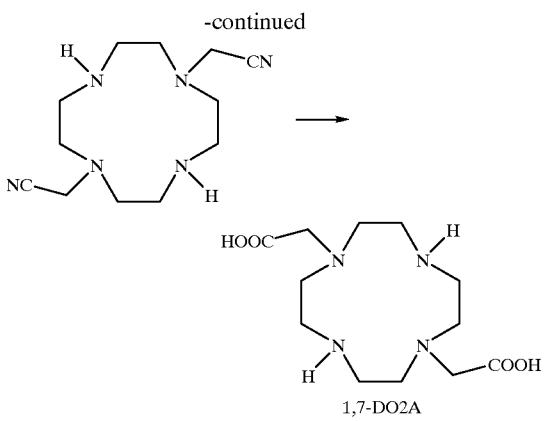

1,7-DO2A

What stated above clearly shows that any direct synthetic routes for the preparation of DO3A or 1,7-DO2A or, in general, of 1,4,7,10-tetraazacyclododecane (III) trisubstituted or disubstituted derivatives would, on one hand, be a remarkable improvement in the processes for the synthesis of Gadoteridol and Gadobutrol and, on the other hand, open a way to the preparation of possible novel complexes for MRI, which are, at present, available with difficulty due to the above cited synthetic problems.

It has now surprisingly been found, and this is the object of the present invention, that the novel compound (I), synthesized starting from compound (II), according to the following Scheme 1:

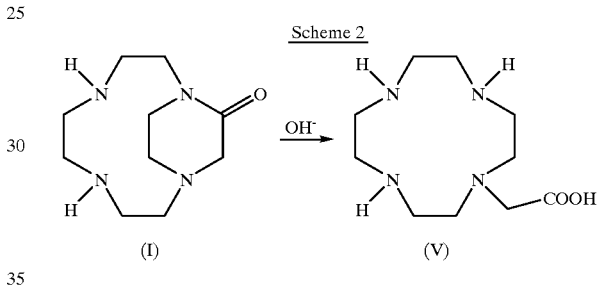

wherein compound (II) is reacted with piperazine at controlled pH to give compound (I), is a useful intermediate for the preparation of 1,4,7,10-tetraazacyclododecane-1,4,7,10-tetraacetic acid derivatives.

Contrary to what described in literature by Weisman (Tetrahedron Letters, 1980, 21, 335) and by Kolinski (Tetrahedron Letters, 1981, 22, 2217), compound (II) is highly reactive also in hydrolytic conditions.

The conversion of (II) to (I) involves heating (II) in aqueous solution at temperatures from 80 to 100° C., at pH slightly acidic, neutral or slightly basic (pH 5–9), and in the presence of piperazine, added in amounts ranging from 2 to 20 mol/mol of (II).

At the end of the reaction, the mixture is alkalinized, concentrated to dryness and extracted with toluene. The toluene solution is partially concentrated and cooled to separate piperazine, which is filtered and can be purified and recycled.

Toluene mother liquors are further concentrated, to obtain (I), which can be recrystallized, for example, from toluene.

Alternatively, at the end of the reaction, the inorganic anions can be removed by ion-exchange. Eluates are suitably concentrated and added with orthophosphoric acid to pH 6.5, thereby precipitating piperazine.$H_3PO_4$ salt. After filtration, the residual phosphate ions are removed from mother liquors by a second ion-exchange, eluates are concentrated to a residue which is recrystallized from toluene, to obtain (I) at high purity.

Compound (I) showed an extremely interesting reactivity, in particular it can be used for the preparation of 1,4,7,10-tetraazacyclododecane (III) variously substituted derivatives, avoiding the step of formation of (III) itself, which is, on the contrary, mandatory when following the procedure at present available in literature.

Compound (I) is a lactam with a 6 atoms cycle and should therefore be remarkably stable in hydrolysis conditions.

Surprisingly, compound (I) is converted by basic hydrolysis, in not quite drastic conditions, to 1,4,7,10-tetraazacyclododecane-1-acetic acid of formula (V), i.e. to a N-monofunctionalized derivative of compound (III), according to the following Scheme 2:

Scheme 2

Compound (I) can be hydrolysed in aqueous basic solution by heating to temperatures from 60 to 100° C., at pH higher than 12.

It is a further object of the present invention the process for the preparation of the compounds of formula (VII) starting from compound (V), obtained according to the process represented in Scheme 2, by alkylation, according to known methods, with an excess of an R—CH(X)—COY alkylating agent of formula (VI), optionally followed by hydrolysis of the ester groups present, represented in the following Scheme 3:

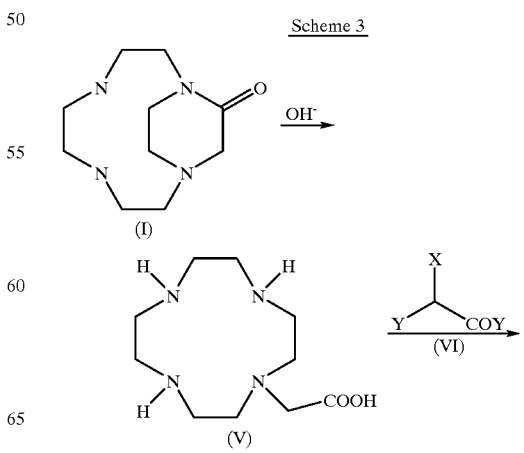

-continued

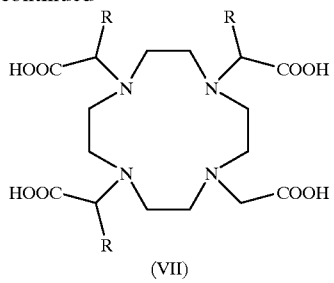

(VII)

in which

R is a hydrogen atom, a straight, branched or cyclic $C_1$–$C_6$ alkyl group, unsubstituted or substituted with 1 to 10 oxygen atoms, or a $C_1$–$C_{20}$ alkyl group, optionally interrupted by a phenylene, phenyloxy or phenylenedioxy, in its turn substituted with a straight or branched $C_1$–$C_6$ alkyl group, unsubstituted or substituted with 1 to 7 hydroxy groups or with 1 to 3 $C_1$–$C_7$ groups;

the aromatic group can be unsubstituted or substituted with alkoxy groups or halogens, carboxy, carbamoyl, alkoxycarbonyl, sulfamoyl, hydroxyalkyl, amino, acylamino, acyl, hydroxyacyl groups;

X is a halogen or a sulfonic acid reactive residue, and

Y is a —OH or —$OR_1$ group, wherein $R_1$ is a straight or branched $C_1$–$C_4$ alkyl group, when Y is the same as —$OR_1$ the ester groups are also hydrolysed, according to known methods, to obtain the compounds of formula (VII).

The alkylating agents (VI) corresponding to compound R—CH(X)—COOH of formula (VIII), and in which X is bromine or chlorine, are preferred, particularly preferred being the alkylating agents of formula (VIII), in which R is a hydrogen atom, corresponding to compound of formula (VIIIa), $XCH_2COOH$, in which X is bromine or chlorine.

In the other cases, the alkylating agent (VI) can be selected from the compounds which either are already commercially available or can be prepared as already described in literature (see for example WO 93/24469 or EP 325762), or by using, for example, known methods for the preparation of suitable precursors (e.g., for acid chlorides α-halogen derivatives see: Harpp et al., J. Org. Chem., 40, 3420, 1975), and subsequent transformation into the desired product.

Preferably, the R group can be selected from the group consisting of: H or a straight or branched alkyl group, such as a methyl, ethyl, propyl, isopropyl, butyl, isobutyl group, in its turn substituted with hydroxy groups or interrupted by oxygen atoms, as defined above.

When an aromatic group is present in R, particularly preferred are: phenyl, benzyl, phenylmethoxymethyl groups.

Particularly preferred are 3-(phenylmethoxy)propanoic acid reactive derivatives, such as 2-bromo-3-(phenylmethoxy)propanoic acid, the preparation of which is described in Grossman et al., Chem. Ber., 91, 538, 1958, and 2-chloro-3-(phenylmethoxy)propanoic acid (CAS RN 124628-32-6), prepared analogously to the brominated derivative.

On the other hand, the $R_1$ group is preferably selected from methyl, ethyl, isopropyl, butyl, tert-butyl.

The reactive group X can be selected, by way of example, from the group consisting of halogens (Cl, Br, I), or it is the mesylate group ($MeSO_2O^-$), the benzenesulfonyloxy group ($PhSO_2O^-$), the nitrobenzenesulfonyloxy group (p—$NO_2PhSO_2O^-$), the tosylate group ($TsO^-$), the triflate group ($CF_3SO_3^-$).

Particularly preferred are the compounds in which X is a halogen, more particularly a bromide or a chloride.

The alkylation of compound (V), when Y is a hydroxyl, can be conveniently performed with reactive derivatives of secondary carboxylic acid, such as 2-bromopropionic acid, in aqueous alkali solution, at temperatures from 25 to 55° C.

Particularly preferred are the alkylating agents of formula (VI), in which Y is a hydroxyl, corresponding to bromoacetic acid (commercially available product), 2-bromopropionic acid (commercially available product), 2-bromobutyric acid (commercially available product).

When the alkylation reaction is carried out with an ester derivative of compound (VIII), the reaction solvent can suitably be selected from dipolar aprotic solvents, in particular from dimethylformamide (DMF), dimethylacetamide (DMA), dimethylsulfoxide (DMSO), acetonitrile ($CH_3CN$) and N-methylpyrrolidone, and the reaction is carried out in the presence of an organic base, preferably an aliphatic tertiary amine selected from triethylamine (TEA), diisopropylethylamine (DIPEA) and tributylamine.

In this case, it can be convenient to transform also the acid group present in compound (V) into the ester group —$OR_1$, to promote the alkylation reaction, depending on the reactivity of the alkylating agent itself.

The reaction temperature can range, in this case, from 0 to 80° C., in any case depending on the reactivity of the selected alkylating agent.

In this case, the alkylation reaction will be followed by a basic hydrolysis of the resulting triester, in conventional conditions, to obtain the desired compound of formula (VII).

The process of the present invention for the preparation of derivatives (VII), bearing three substituents corresponding to formula —CH(R)COOH and one —$CH_2COOH$ substituent, is a brilliant, economically advantageous solution to the problem of differentiating the four nitrogen equivalent sites.

Compounds of this type, useful for the preparation of contrast agents for diagnosis by nuclear magnetic resonance, have already been described, for example, in EP 325,762.

The preparation of these compounds according to the process of the present invention is economically more convenient and industrially more efficient, as it involves no use of compound (III) as starting substrate, which has a prohibitive cost (ranging from 67,000 to 98,000 Italian Lire per gram, depending on the manufacturer).

By way of example of the huge potentialities given by this synthetic route, the synthesis of the novel compound, α,α', α"-tris(methyl)-1,4,7,10-tetraazacyclododecane-1,4,7,10-tetraacetic acid, is reported in Experimental section:

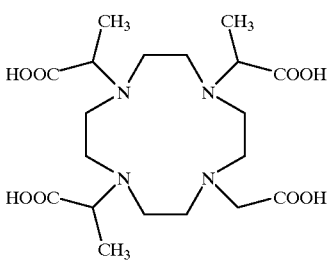

as well as that of α,α',α"-tris[(phenylmethoxy)methyl]-1,4,7,10-tetraazacyclododecane-1,4,7,10-tetraacetic acid

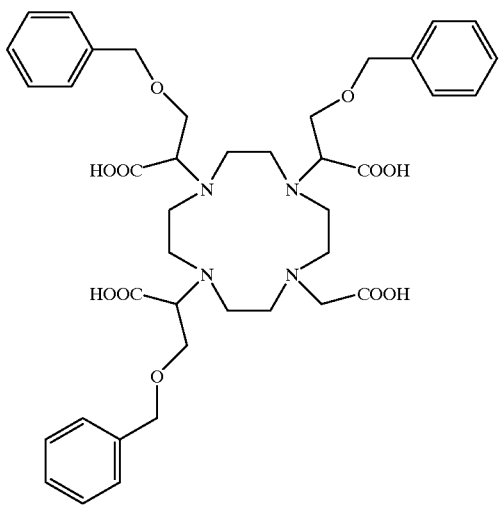

which, by catalytic hydrogenation, as described in example 6 of the cited Patent, yields α,α',α"-tris(hydroxymethyl)-1,4,7,10-tetraazacyclododecane-1,4,7,10-tetraacetic acid.

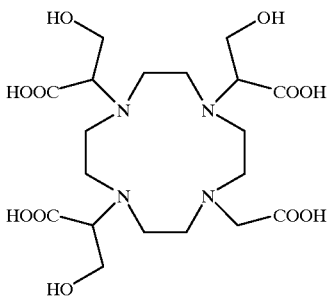

Particularly preferred is the process according to scheme 4 for the preparation of 1,4,7,10-tetraazacyclododecane-1,4,7,10-tetraacetic acid by alkylation with the alkylating agent (VIIIa), so as to directly synthesize DOTA starting from compound (I), according to the following scheme:

Scheme 4

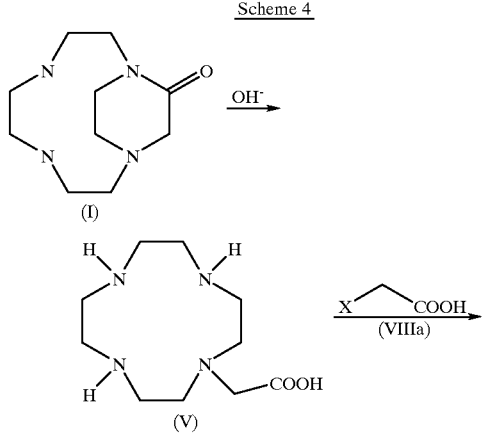

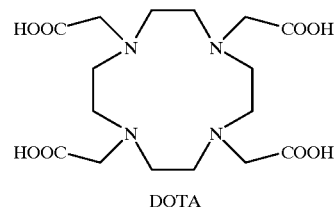

DOTA in which X, Y have the meanings defined above.

Compound (V) can, in fact, be easily alkylated with chloro- or bromoacetic acid, in aqueous alkaline solution, at temperatures from 25 to 55° C.

It is a further object of the invention an alternative process for the preparation of the compounds (VII), as represented in Scheme 5, starting from compound (I)

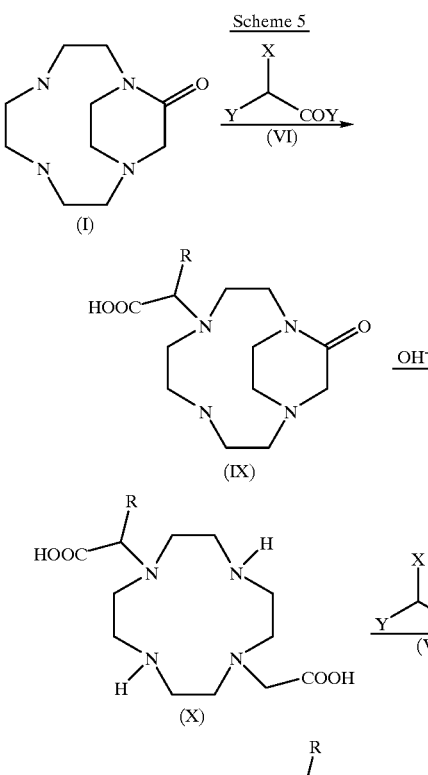

through a selective monoalkylation reaction, according to known methods, at controlled pH, with the alkylating agent (VI) as defined above, to give compound (X), which can subsequently be alkylated with the alkylating agent (VI) to give compounds (VII).

It is a further object of the present invention the process for the preparation of the compounds of formula (XII), as represented in Scheme 6, starting from compound (X), obtained according to the process represented in Scheme 5

Scheme 6

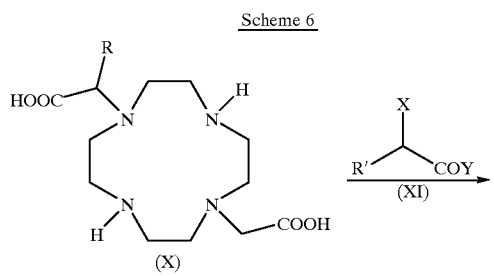

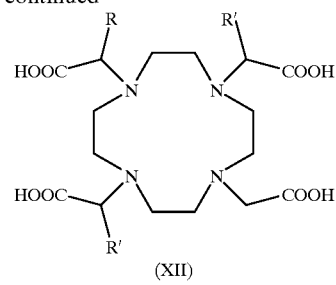

in which compound (X) is alkylated, according to known methods, with the alkylating agent (XI) in which R', independently of R, has the same meanings as R.

An example of the possibilities given by this novel process is the preparation of α1,α7-bis[(phenylmethoxy)methyl]-α4-methyl-1,4,7,10-tetraazacyclododecane-1,4,7,10-tetraacetic acid which, after catalytic hydrogenation, gives the debenzylated analogue.

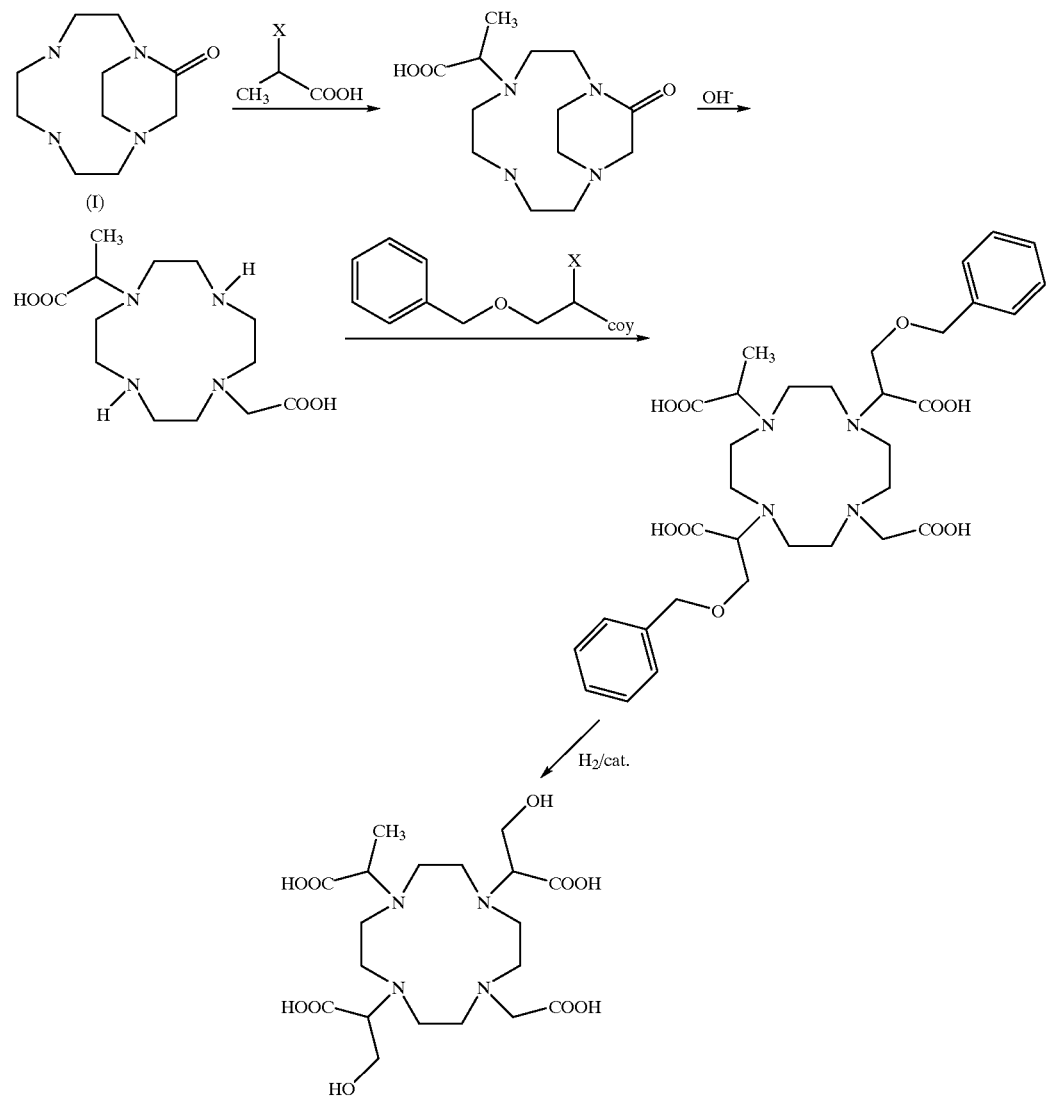

Particularly preferred is the preparation of 1,7-DO2A, according to scheme 5, through formation of the novel compound 12-oxo-1,4,7,10-tetraazabicyclo(8.2.2] tetradecane-4-acetic acid of formula (XIII), which is subjected to basic hydrolysis to give 1,7-DO2A, i.e. 1,4,7,10-tetraazacyclododecane-1,7-diacetic acid, as represented in Scheme 7

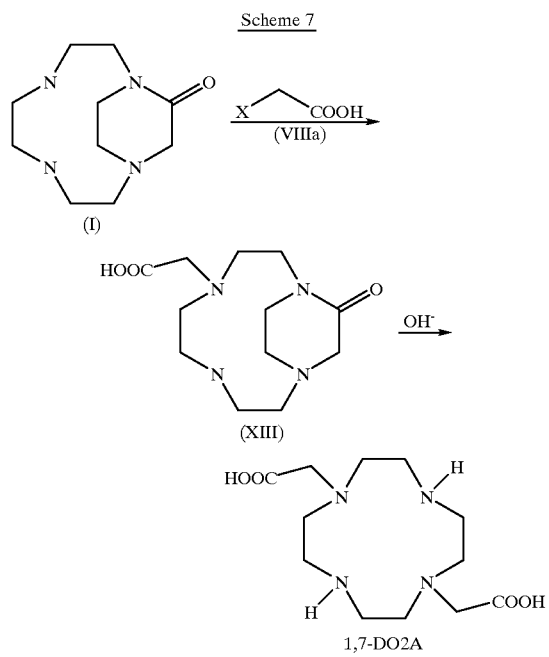

Compound (I) can be selectively carboxymethylated in aqueous solution, for example with bromoacetic acid (1 mol) at pH 12.5 and at temperatures from 15 to 25° C., or in dimethylacetamide in the presence of sodium carbonate (1 mol) or of diisopropylethylamine, or in ethanol and sodium hydroxide: the resulting intermediate (XIII) can be transformed into 1,7-DO2A by basic hydrolysis at pH higher than 13 and at temperatures from 80 to 100° C.

1,7-DO2A can, in its turn, be transformed into DOTA by reaction with the alkylating agent of formula (VIIIa).

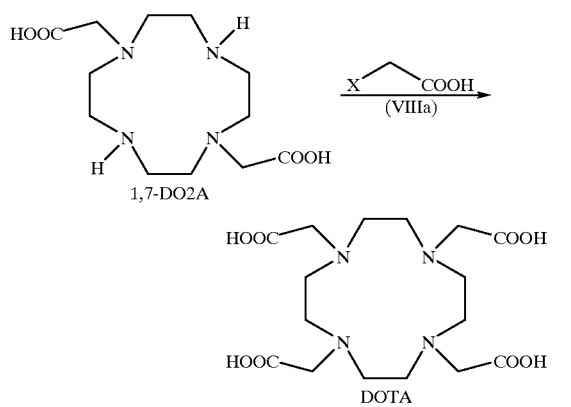

The conditions used, for example, for the alkylating agent (VIIIa) comprise carrying out the reaction in aqueous solution, at pH 10–12 and at temperatures from 25 to 50° C.

According to the process represented in Scheme 6, when the alkylating agent (VI) corresponds to the alkylating agent (VIII), compounds of formula (XIV) can be prepared, as represented in Scheme 8:

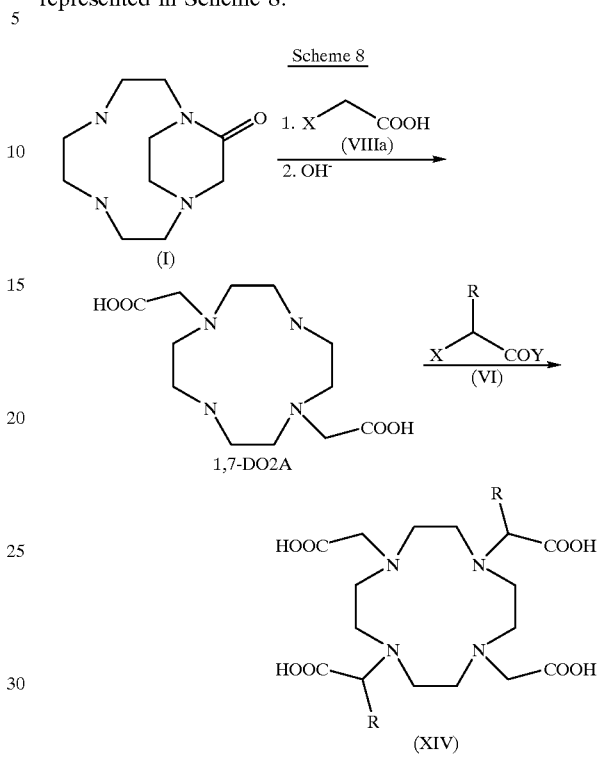

in which R, X and Y have the meanings defined above.

When R in the alkylating agent (VI) is the phenyl-methoxymethyl group, it is possible to prepare, by using the alkylating agents preferred for this type of substituent defined above, α1,α7-bis[(phenylmethoxy)methyl]-1,4,7,10-tetraazacyclododecane-1,4,7,10-tetraacetic acid, already described in EP 325,762, and its debenzylated analogue upon catalytic hydrogenation.

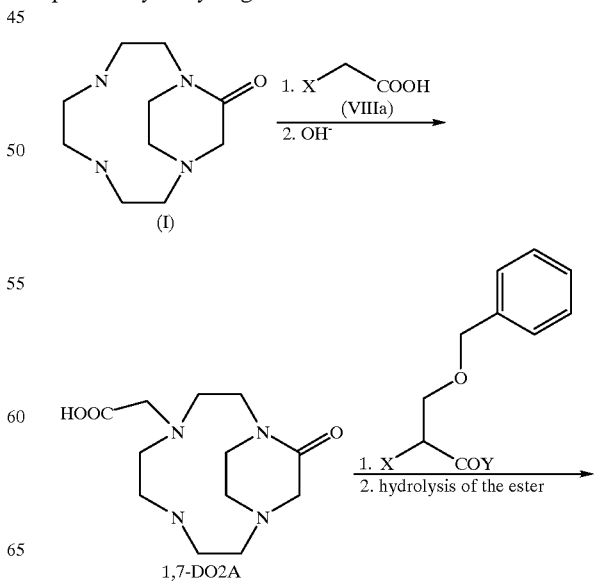

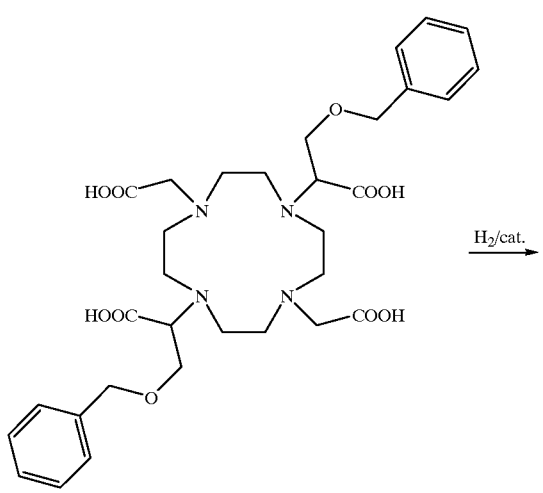

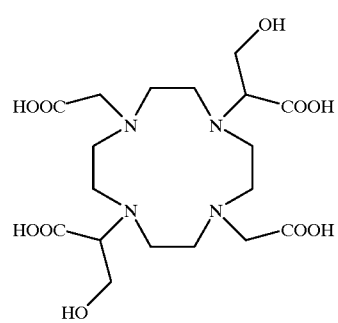

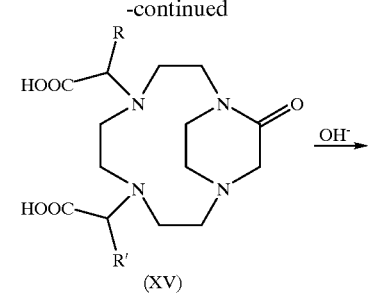

(XV)

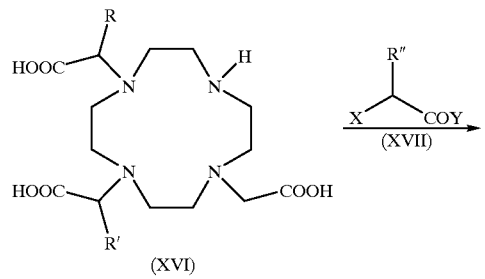

(XVI)

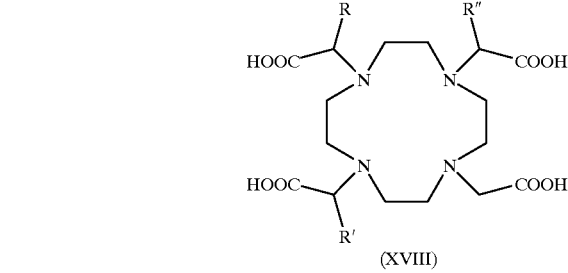

(XVIII)

Again starting from compound (I), it is also possible to perform the complete differentiation of the four nitrogen atoms of tetraazacyclododecane, to give compounds (XVIII), according to the following Scheme 9:

Scheme 9

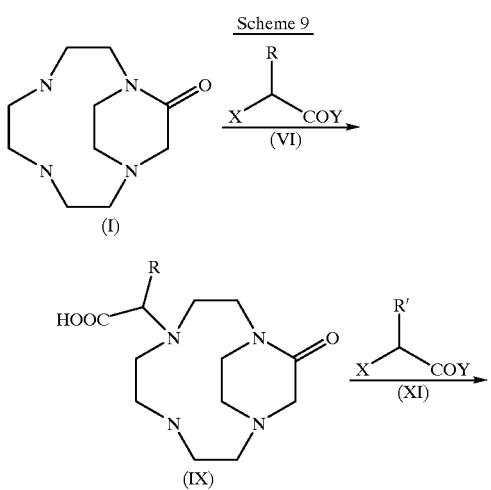

in which X, Y have the meanings defined above and R, R', R" have independently the same meanings.

An example of said synthetic approach is the preparation of α1-[(phenylmethoxy)methyl]-α4-methyl-α7-ethyl-1,4,7,10-tetraazacyclododecane-1,4,7,10-tetraacetic acid and of its debenzylated analogue, after catalytic hydrogenation.

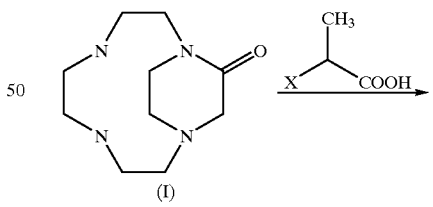

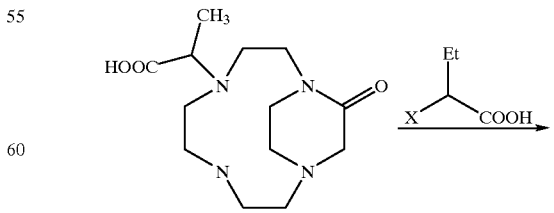

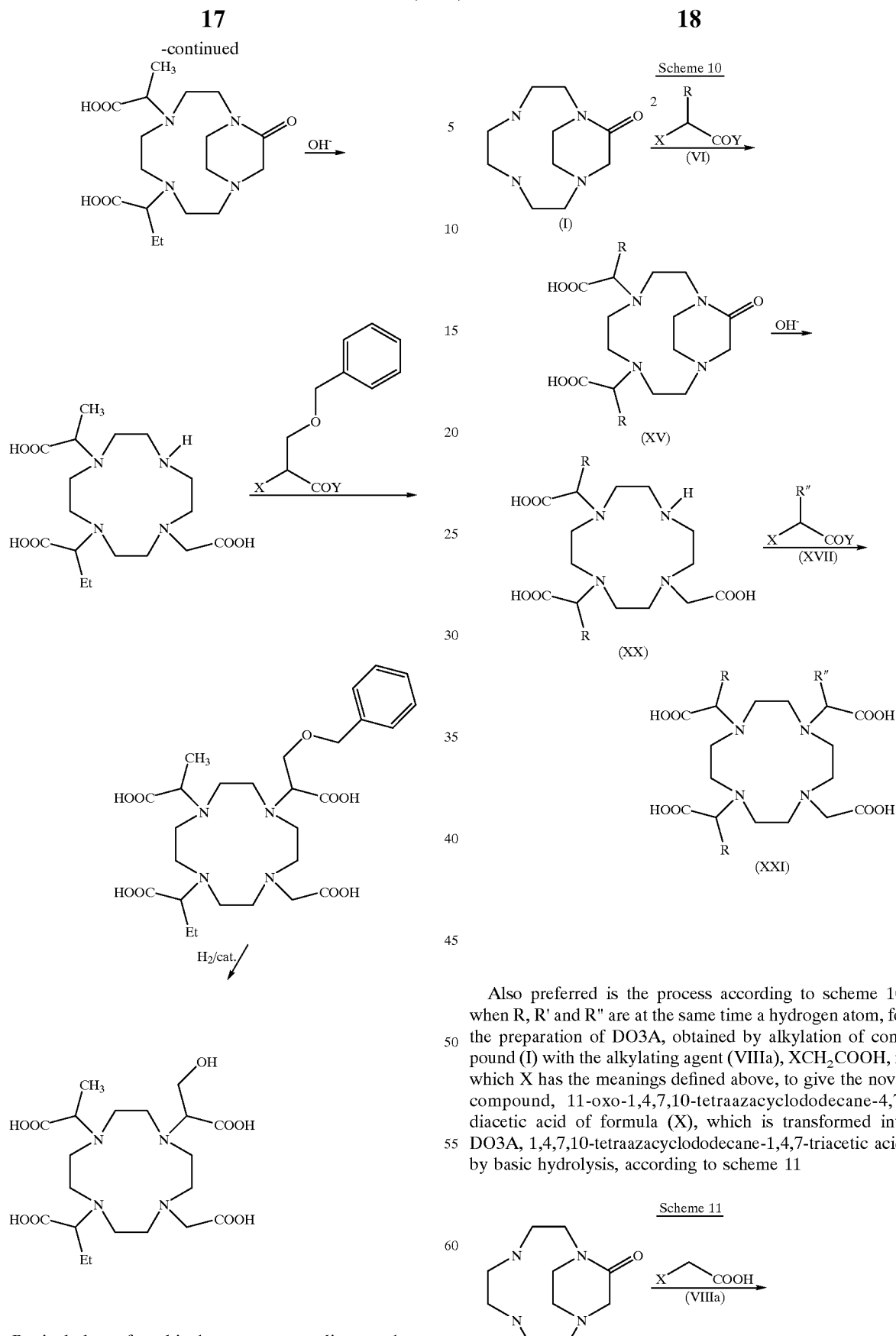

Particularly preferred is the process according to scheme 9, in which R and R' have the same meanings, represented in the following Scheme 10

Also preferred is the process according to scheme 10, when R, R' and R" are at the same time a hydrogen atom, for the preparation of DO3A, obtained by alkylation of compound (I) with the alkylating agent (VIIIa), $XCH_2COOH$, in which X has the meanings defined above, to give the novel compound, 11-oxo-1,4,7,10-tetraazacyclododecane-4,7-diacetic acid of formula (X), which is transformed into DO3A, 1,4,7,10-tetraazacyclododecane-1,4,7-triacetic acid, by basic hydrolysis, according to scheme 11

-continued

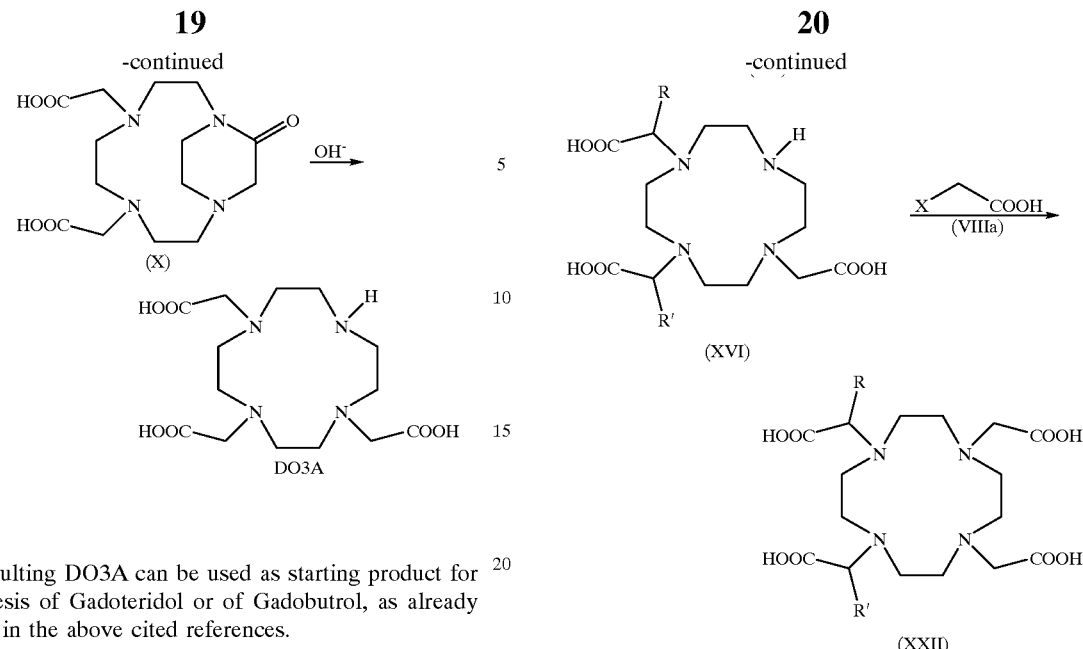

The resulting DO3A can be used as starting product for the synthesis of Gadoteridol or of Gadobutrol, as already described in the above cited references.

The compound (I) can be directly transformed into intermediate (X) by reaction with 2 moles of the alkylating agent (VIIIa), in aqueous solution, at pH 13 and at a temperature from 25 to 45° C.

Compound (X) can be converted to DO3A by basic hydrolysis at pH higher than 13 and at temperatures from 80 to 100° C.

A further aspect of the process according to scheme 9, in which the alkylating agent (XVII) corresponds to that of formula (VIII), relates to the possibility to selectively obtain 1,4,7,10-tetraazacyclododecane-1,4-diacetic acid derivatives, of formula (XXII), as represented in the following Scheme 12.

An example of this synthetic scheme is the preparation of α4-methyl-α7-methyl-1,4,7,10-tetraazacyclododecane-1,4,7,10-tetraacetic acid.

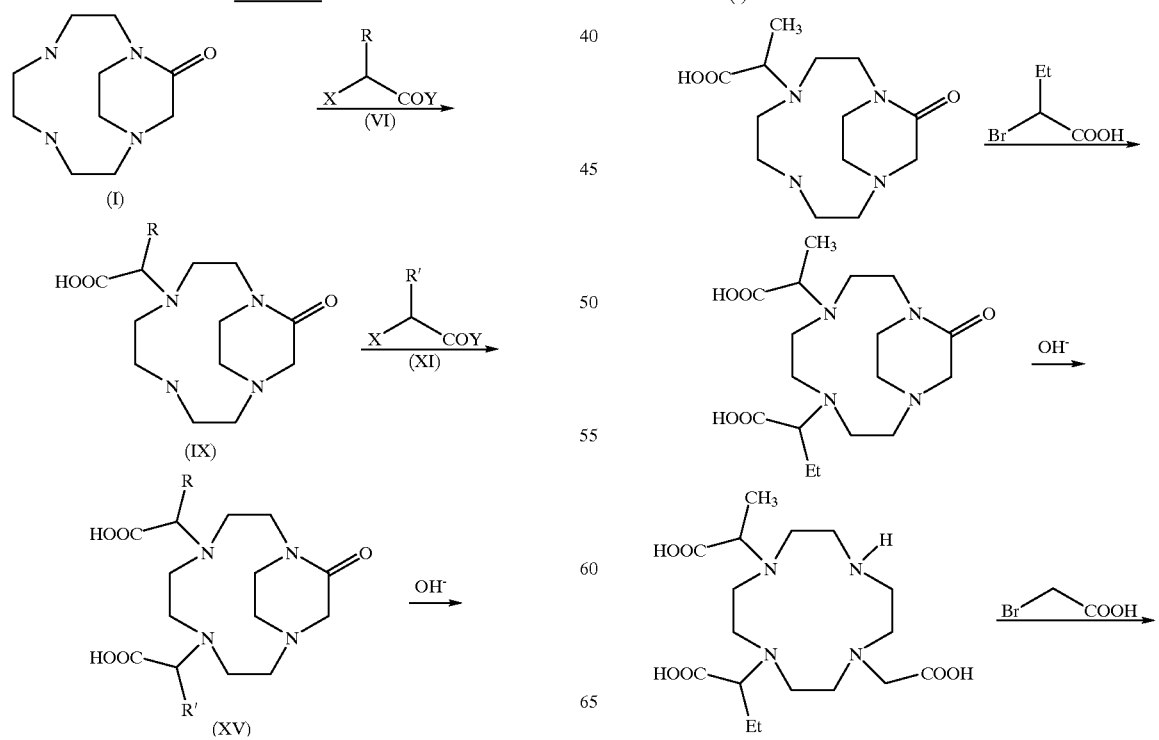

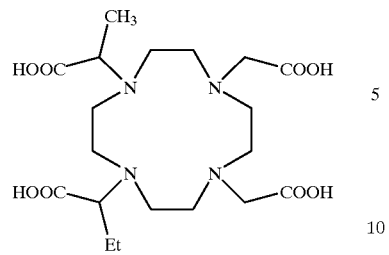

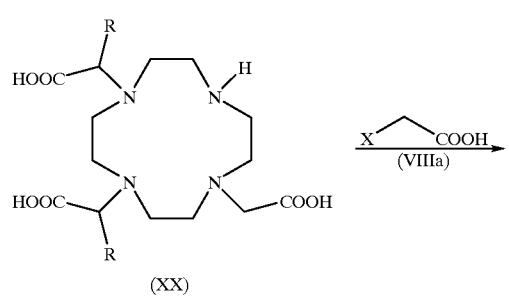

Also preferred is the process, according to scheme 9, for the preparation of the compounds of formula (XXIII), in which R and R' have the same meaning and the alkylating agent (XVII) corresponds to that of formula (VIIIa), represented in the following Scheme 13.

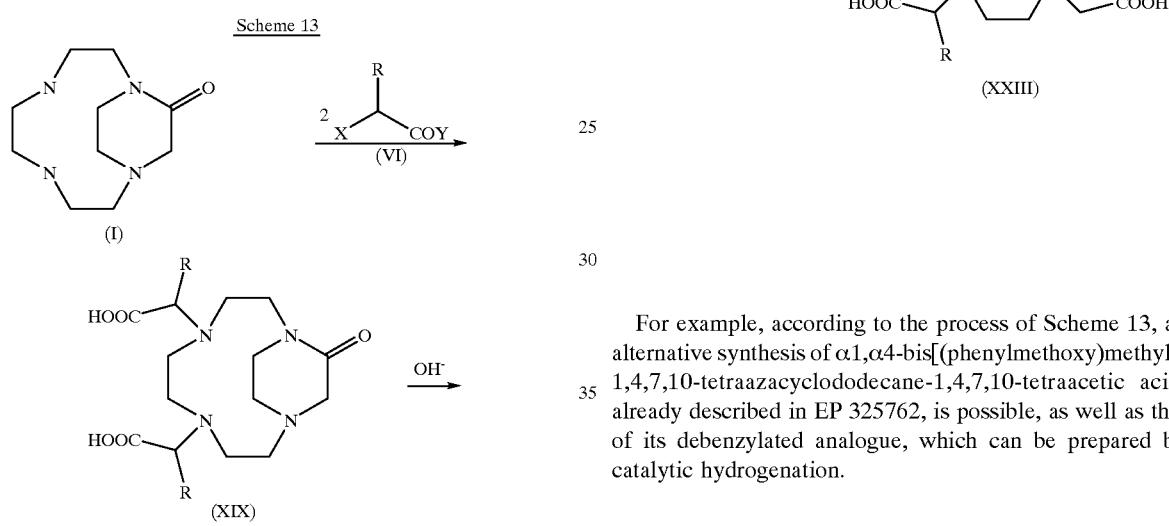

Scheme 13

For example, according to the process of Scheme 13, an alternative synthesis of α1,α4-bis[(phenylmethoxy)methyl]-1,4,7,10-tetraazacyclododecane-1,4,7,10-tetraacetic acid, already described in EP 325762, is possible, as well as that of its debenzylated analogue, which can be prepared by catalytic hydrogenation.

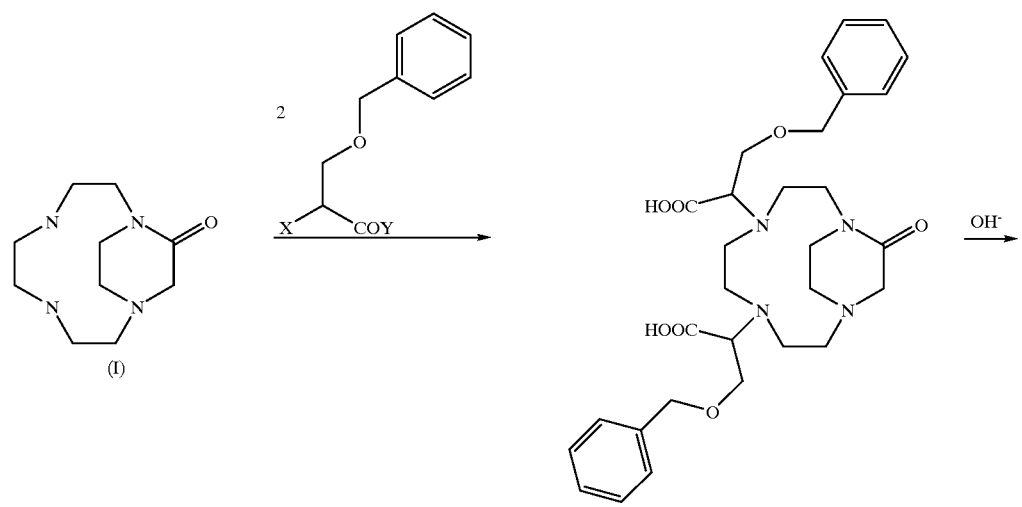

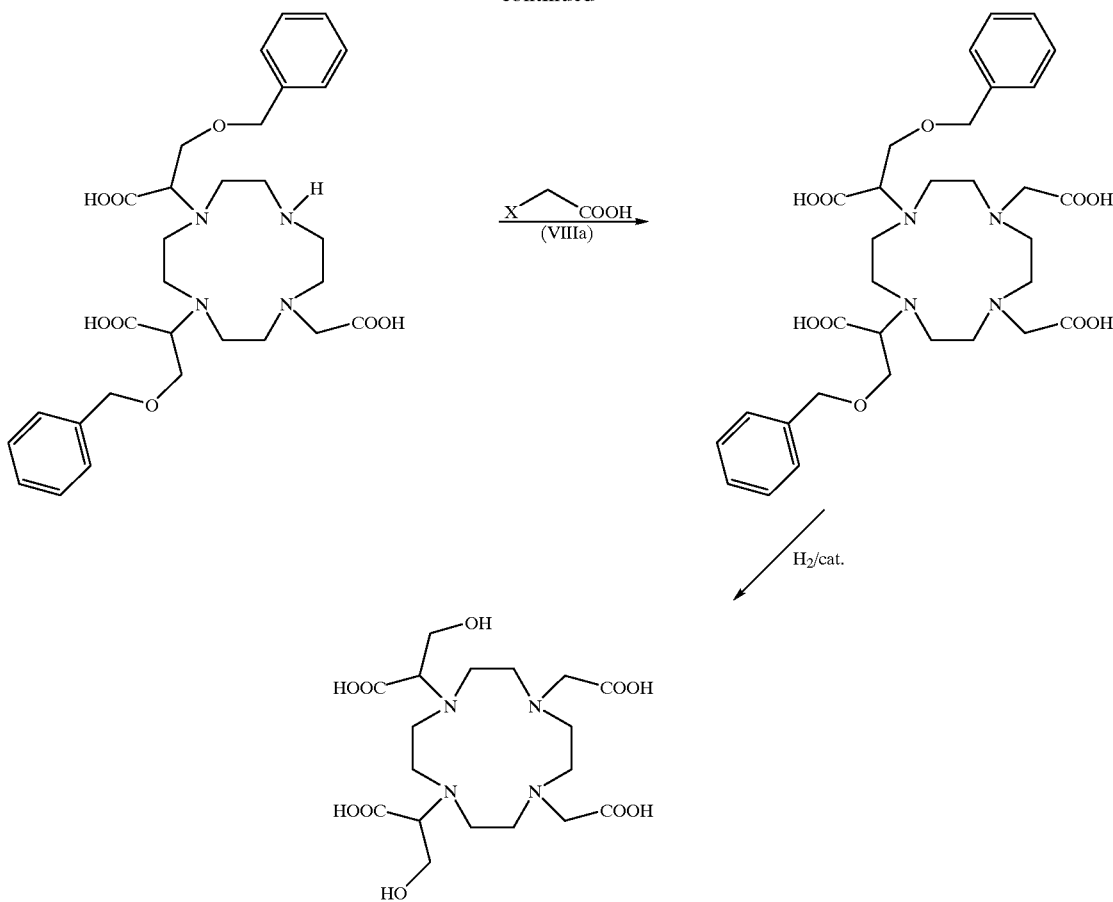

In substance, compound (I) is a synton useful to obtain 1,4,7,10-tetraazacyclododecane (TAZA) derivatives both mono-, and di-, tri- or tetrasubstituted (symmetrically or asymmetrically), without the trouble-some use of the macrocycle itself as starting product.

In the following, some examples of preparation according to the method of the present invention are reported.

Experimental section

EXAMPLE 1

Synthesis of 1,4,7,10-tetraazabicyclo[8.2.2]tetradodecan-2-one (I)

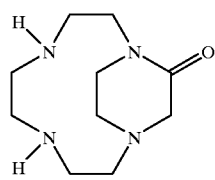
(I)

500 g (2.54 mol) of 2α,4α,6α8α-decahydrotetraazacyclopent[fg]acenaphthylene, prepared as described in MI96A001257, are dissolved in 4 L of water. 3.9 kg (20.0 mol) of piperazine hexahydrate are added and pH is adjusted to 6 with conc. HCl (about 2.86 kg). The solution is refluxed for 24 h, then cooled to room temperature, percolated on 22 L of anionic exchanger resin Relite 3AS/FB (Resindion) and the column is washed with deionized water. The fractions containing the product are concentrated at reduced pressure to a volume of 8 L, then cooled to 5° C. and slowly added with 2.34 kg (20.0 mol) of 84% w/w orthophosphoric acid to pH 6.5. After 1 h, the precipitated solid (piperazine.$H_3PO_4$) is filtered and washed on the filter with water precooled at 5° C. The washings are added to the filtrate, which is percolated on 2 L of anionic exchanger resin Relite 3AS/FB (Resindion), then concentrated to dryness at reduced pressure and redissolved in hot toluene. Insolubles are filtered off. The toluene solution is concentrated to 1 kg weight and cooled to 5° C. After 12 h the crystallized solid is filtered and washed on the filter with some cold toluene. The resulting product, after drying at 50° C. under vacuum, weighs 388 g.

Yield: 72%

Humid piperazine.$H_3PO_4$ is dried at 50° C. under vacuum to obtain 3.8 kg of piperazine.$H_3PO_4$ (water content: 9%).

Recovery yield: 95%

The $^1$H-NMR, $^{13}$C-NMR, IR and MS spectra are consistent with the indicated structure.

EXAMPLE 2

Synthesis of 1,4,7,10-tetraazacyclododecane-1-acetic acid (V)

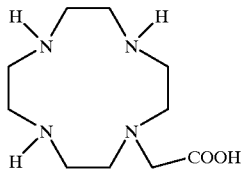

(V)

10 g of 1,4,7,10-tetraazabicyclo[8.2.2]tetradodecan-2-one (0.047 mol), prepared according to Example 1, are dissolved in 30 g of 10% w/w NaOH. The solution is heated at 100° C. for 8 h, then cooled to room temperature, diluted with 70 g of water and percolated on a column containing 150 ml of cationic exchanger resin Duolite C20MB (Rohm & Haas), eluting with 2N ammonia, to collect about 1 L of eluate, which is concentrated to dryness at reduced pressure and at a temperature of 50° C. The crude product is redissolved in 30 g of water and treated with 11 g of conc. sulfuric acid. The solution is cooled to 5° C. and added with 60 g of acetone. After 6 h the mixture is filtered and the solid is washed with an acetone/water=2/1 w/w mixture. After drying at 50° C. under vacuum, 18.2 g of 1,4,7,10-tetraazacyclododecane-1-acetic acid.2H$_2$SO$_4$ are obtained.

Yield: 90.8%

The $^1$H-NMR, $^{13}$C-NMR, IR and MS spectra are consistent with the indicated structure.

EXAMPLE 3

Synthesis of 1,4,7,10-tetraazacyclododecane-1,4,7,10-tetraacetic acid (DOTA)

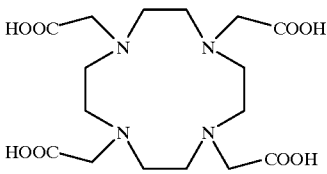

10 g of 1,4,7,10-tetraazabicyclo[8.2.2]tetradodecan-2-one (0.047 mol), prepared according to Example 1, are dissolved in 30 g of 10% w/w NaOH. The solution is heated at 100° C. for 8 h, then cooled to room temperature, diluted with 30 g of water and slowly added with a solution prepared dissolving 22.68 g (0.165 mol) of bromoacetic acid in 40 ml of water. The mixture is reacted at 45° C. for 5 h, keeping pH at 10.5–11 by addition of 2N NaOH, then cooled to room temperature and acidified with conc. HCl to pH 2. After 1 h, the precipitated solid is filtered and washed on the filter with deionized water. The crude product is redissolved in 400 ml of deionized water. The resulting solution is percolated on a column containing 400 ml of polyvinylpyridine resin (PVP), eluting at length with water. The useful fractions are combined and concentrated to dryness under vacuum, then dried in a static drier at 50° C. under vacuum to obtain 17.7 g of DOTA.

Yield: 93%

The $^1$H-NMR, $^{13}$C-NMR, IR and MS spectra are consistent with the indicated structure.

EXAMPLE 4

Synthesis of α,α',α"-tris(methyl)-1,4,7,10-tetraazacyclododecane-1,4,7,10-tetraacetic acid

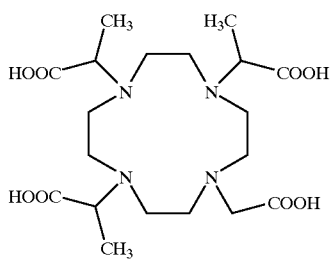

16 g (0.075 mol) of 1,4,7,10-tetraazabicyclo[8.2.2] tetradodecan-2-one, prepared according to Example 1, are dissolved in 50 g of 10% w/w NaOH. The solution is heated at 100° C. for 8 h, then cooled to room temperature, diluted with 45 g of water and slowly added with a solution prepared dissolving 45.89 g (0.300 mol) of 2-bromopropionic acid in 40 ml of water. The mixture is reacted at 45° C. for 12 h, keeping pH at 10.5–11 by addition of 2N NaOH, then cooled to room temperature and acidified with conc. HCl to pH 2. After 1 h, the precipitated solid is filtered and washed on the filter with deionized water. The crude product is redissolved in 600 ml of polyvinylpyridine resin (PVP), eluting at length with water. The useful fractions are combined and concentrated to dryness under vacuum, then dried in a static drier at 50° C. under vacuum to obtain 29.2 g of the desired product.

Yield: 87%

The $^1$H-NMR, $^{13}$C-NMR, IR and MS spectra are consistent with the indicated structure.

EXAMPLE 5

Synthesis of α,α',α"-tris[(phenylmethoxy)methyl]-1,4,7,10-tetraazacyclododecane-1,4,7,10-tetraacetic acid

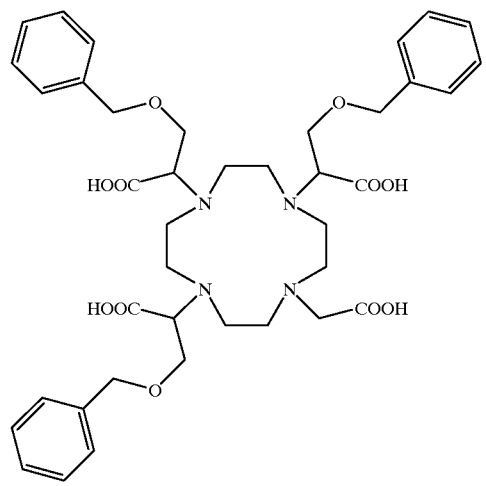

According to the procedure described in example 4, using 1,4,7,10-tetracyclododecane-1-acetic acid (prepared as described in example 2) and 2-bromo-3-(phenylmethoxy) propanoic acid methyl ester or 2-trifluoromethanesulfonate-2-(phenylmethoxy)-propanoic acid methyl ester in DMF and in the presence of triethylamine. The methyl ester is hydrolysed to obtain the desired product.

The $^1$H-NMR, $^{13}$C-NMR, IR and MS spectra are consistent with the indicated structure.

EXAMPLE 6

Synthesis of α,α',α"-tris(hydroxymethyl)-1,4,7,10-tetraazacyclododecane-1,4,7,10-tetraacetic acid

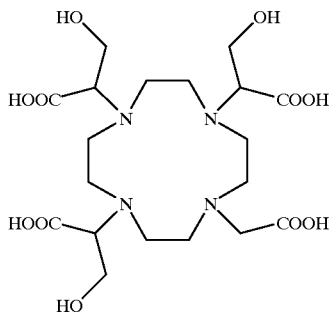

The product obtained in Example 5 is subjected to catalytic hydrogenation in the presence of 5% Pd-on-charcoal, to obtain, after absorption of the necessary amount of hydrogen, the desired product.

The $^1$H-NMR, $^{13}$C-NMR, IR and MS spectra are consistent with the indicated structure.

EXAMPLE 7

Synthesis of 12-oxo-1,4,7,10-tetraazabicyclo[8.2.2]tetradecane-4-acetic acid (XIII)

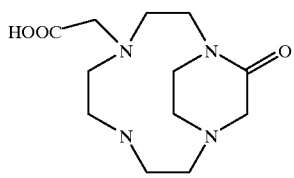

(XIII)

50 g (0.235 mol) of 1,4,7,10-tetraazabicyclo[8.2.2]tetradodecan-2-one, prepared according to Example 1, are dissolved in 500 ml of deionized water. 36 g (0.259 mol) of bromoacetic acid are added, pH is adjusted to 12.5 by addition of 1N NaOH and the mixture is reacted at room temperature for 12 h, keeping pH at 12.5 through gradual additions of 1N NaOH. The mixture is then cooled and percolated on a column containing 1 L of cationic exchanger resin Duolite C20MB (Rohm & Haas). The column is repeatedly washed with deionized water, then eluted with 2N ammonia. The fractions containing the product are combined and concentrated at reduced pressure to a solid residue, which is redissolved in 500 ml of deionized water. The resulting solution is percolated on a column containing 5 L of resin Amberlite XAD 1600, and eluted with water. The fractions containing the pure product are combined and concentrated to dryness at reduced pressure, then dried in a static drier at 50° C. under vacuum, to obtain 49.5 g (0.183 mol) of 12-oxo-1,4,7,10-tetraazabicyclo[8.2.2]tetradecane-4-acetic acid.

Yield: 78%

The $^1$H-NMR, $^{13}$C-NMR, IR and MS spectra are consistent with the indicated structure.

EXAMPLE 8

Synthesis of α1,α7-bis((phenylmethoxy)methyl)-α4-methyl-1,4,7,10-tetraazacyclododecane-1,4,7,10-tetraacetic acid

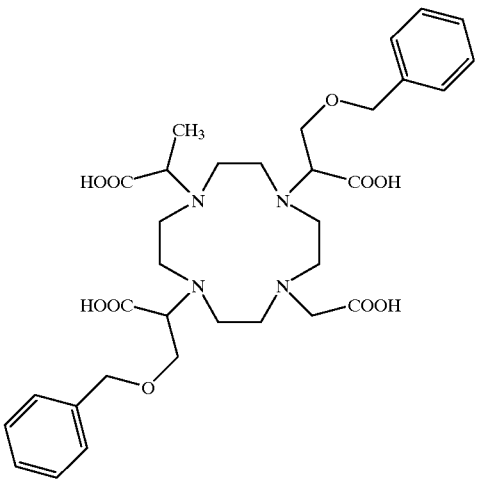

A) Preparation of 12-oxo-1,4,7,10-tetraazabicyclo[8.2.2]tetradecane-α4-methyl-4-acetic acid

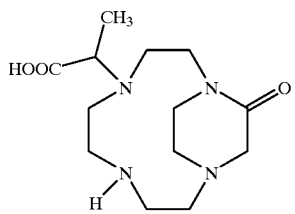

The product is prepared analogously to the procedure of Example 7, using the 2-bromopropionic acid instead of bromoacetic acid, to obtain the desired product.

The $^1$H-NMR, $^{13}$C-NMR, IR and MS spectra are consistent with the indicated structure.

B) α4-Methyl-1,4,7,10-tetraazacyclododecane-1,7-diacetic acid.

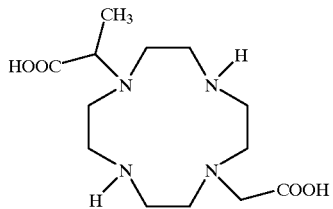

According to the procedure described in example 2 the desired product is obtained by basic hydrolysis of the product obtained at the preceding step.

The $^1$H-NMR, $^{13}$C-NMR, IR and MS spectra are consistent with the indicated structure.

C) α1,α4-bis[(phenylmethoxy)methyl]-α7-methyl-1,4,7,-10-tetraazacyclododecane-1,4,7,10-tetraacetic acid According to the procedure described in example 5, the product from the preceding step is alkylated with 2-bromo-3-(phenylmethoxy)propanoic acid methyl ester or with 2-trifluoromethanesulfonate-3-(phenylmethoxy)propanoic acid methyl ester. The diester is hydrolysed to obtain the desired product.

The $^1$H-NMR, $^{13}$C-NMR, IR and MS spectra are consistent with the indicated structure.

EXAMPLE 9

Synthesis of α1,α7-bis(hydroxymethyl)-α4-methyl-1,4,7,10-tetraazacyclododecane-1,4,7,10-tetraacetic acid

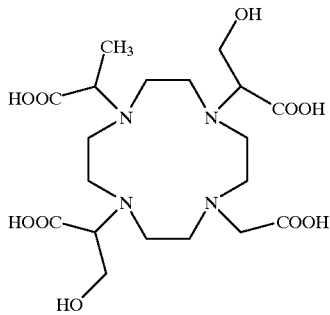

According to the procedure described in Example 6, the product described in example 8 is subjected to catalytic hydrogenation, to obtain the desired product.

The $^1$H-NMR, $^{13}$C-NMR, IR and MS spectra are consistent with the indicated structure.

EXAMPLE 10

Synthesis of 1,4,7,10-tetraazacyclododecane-1,7-diacetic acid (1,7-DO2A)

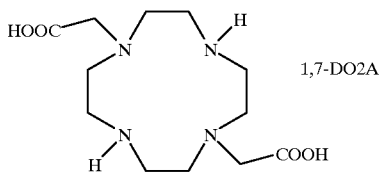

20 g (0.074 mol) of 12-oxo-1,4,7,10-tetraazabicyclo[8.2.2]tetradecane-4-acetic acid, prepared as described in example 5, are dissolved in 88.8 g of 10% NaOH. The solution is refluxed overnight, then cooled and acidified to pH 12 by addition of conc. HCl. The resulting solution is percolated on a column containing 600 ml of anionic exchanger resin IRA420 (Rohm & Haas), which is washed repeatedly with water, then eluted with 1N HCl. The fractions containing the product are combined and concentrated at reduced pressure to a volume of about 500 mL. The solution is percolated on a column containing 2 L of polyvinylpyridine resin (PVP), eluting with water, the fractions containing the desalted product are collected, combined and concentrated to dryness under vacuum. The crude solid is recrystallized from methanol/acetone=8/2, finally dried in a static drier at 50° C. under vacuum. 18.5 g (0.064 mol) of 1,4,7,10-tetraazacyclododecane-1,7 -diacetic acid are obtained.

Yield: 86%

The $^1$H-NMR, $^{13}$C-NMR, IR and MS spectra are consistent with the indicated structure.

EXAMPLE 11

Synthesis of 1,4,7,10-tetraazacyclododecane-1,7-diacetic acid (1,7-DO2A)

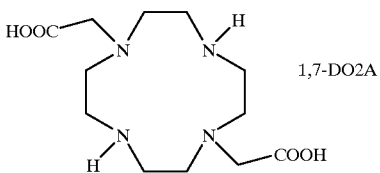

50 g (0.235 mol) of 1,4,7,10-tetraazabicyclo[8.2.2]tetradodecan-2-one, prepared according to Example 1, are dissolved in 500 ml of deionized water. 36 g (0.259 mol) of bromoacetic acid are added, pH is adjusted to 12.5 by addition of 1N NaOH and the mixture is reacted at room temperature for 12 h, keeping pH at 12.5 through gradual additions of 1N NaOH. pH is adjusted to 14 with NaOH in pellets and the solution is refluxed overnight, then cooled to room temperature and diluted with 500 ml of water. The resulting solution is percolated on a column containing 1 L of cationic exchanger resin C20MB (Rohm & Haas), washing repeatedly with water, then the product is eluted with 2N ammonia. The useful fractions are combined and concentrated to dryness at reduced pressure. The crude solid is redissolved in 1 L of deionized water and the resulting solution is percolated on a column containing 5 L of resin Amberlite XAD1600, eluting with deionized water. The useful fractions are concentrated at reduced pressure to a solid residue, which is finally recrystallized from methanol/acetone=8:2, to obtain 54,9 g (0.190 mol) of 1,4,7,10-tetraazacyclododecane-1,7-diacetic acid.

Yield: 81%

The $^1$H-NMR, $^{13}$C-NMR, IR and MS spectra are consistent with the indicated structure.

EXAMPLE 12

Synthesis of α1,α7-bis[(phenylmethoxy)methyl)]-1,4,7,10-tetraazacyclododecane-1,4,7,10-tetraacetic acid

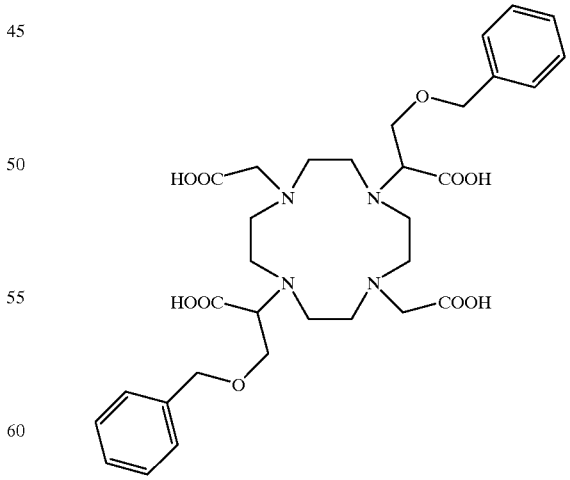

According to the procedure described in example 8C, 1,7-DO2A acid is reacted with 2-bromo-3-(phenylmethoxy)propanoic acid methyl ester or with 2-trifluoromethanesulfonate-3-(phenylmethoxy)propanoic acid methyl ester. The diester is hydrolysed to obtain the desired product.

The $^1$H-NMR, $^{13}$C-NMR, IR and MS spectra are consistent with the indicated structure.

EXAMPLE 13

Synthesis of α1,α7-bis(hydroxymethyl)-1,4,7,10-tetraazacyclododecane-1,4,7,10-tetraacetic acid

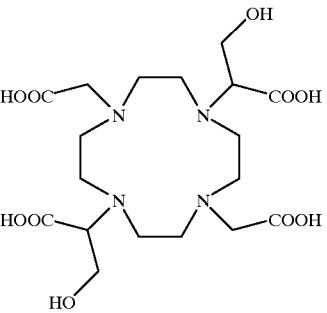

According to the procedure described in example 6, the product described in example 12 is subjected to catalytic hydrogenation to obtain the desired product.

The $^1$H-NMR, $^{13}$C-NMR, IR and MS spectra are consistent with the indicated structure.

EXAMPLE 14

Synthesis of α1-[(phenylmethoxy)methyl)]-α4-methyl-α7-ethyl-1,4,7,10-tetraazacyclododecane-1,4,7,10-tetraacetic acid

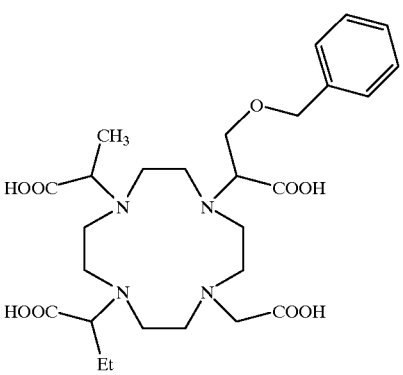

A) α4-Ethyl-α7-methyl-11-oxo-1,4,7,10-tetraazabicyclo [8.2.2]tetradecane-4,7-diacetic acid

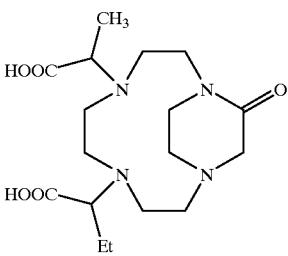

12-Oxo-1,4,7,10-tetraazabicyclo[8.2.2]tetradecane-α4-methyl-4-acetic acid, prepared according to the procedure described in example 8A, is reacted with 2-bromobutanoic acid according to the same procedure.

The $^1$H-NMR, $^{13}$C-NMR, IR and MS spectra are consistent with the indicated structure.

B) α1-Methyl-α4-ethyl-1,4,7,10-tetraazacyclododecane-1, 4,7-triacetic acid

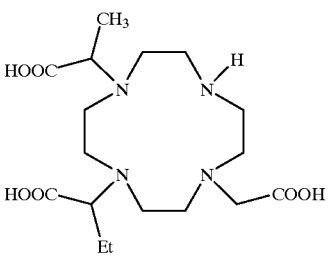

α4-Ethyl-α7-methyl-11-oxo-1,4,7,10-tetraazabicyclo [8.2.2]tetradecane-4,7-acetic acid, prepared in the above step, is hydrolysed according to the procedure described in example 2, to obtain the desired product.

The $^1$H-NMR, $^{13}$C-NMR, IR and MS spectra are consistent with the indicated structure.

C) α1-[(Phenylmethoxy)methyl)]-α4-methyl-α7-ethyl-1,4, 7,10-tetraazacyclododecane-1,4,7,10-tetraacetic acid According to the procedure described in example 8C, α1-methyl-α4-ethyl-1,4,7,10-tetraazacyclododecane-1,4,7-triacetic acid is reacted with 2-bromo-3-(phenylmethoxy) propanoic acid methyl ester in DMF and in the presence of triethylamine. The resulting ester is hydrolysed to obtain the desired product.

The $^1$H-NMR, $^{13}$C-NMR, IR and MS spectra are consistent with the indicated structure.

EXAMPLE 15

Synthesis of α1-ethyl,α4-methyl,α7-(hydroxymethyl)-1, 4,7,10-tetraazacyclododecane-1,4,7,10-tetraacetic acid

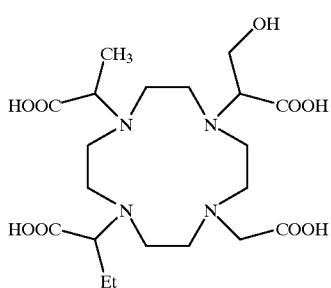

According to the procedure described in Example 6, the product described in example 14 is subjected to catalytic hydrogenation to obtain the desired product.

The $^1$H-NMR, $^{13}$C-NMR, IR and MS spectra are consistent with the indicated structure.

EXAMPLE 16

Synthesis of α4-ethyl,α7-methyl-1,4,7,10-tetraazacyclododecane-1,4,7,10-tetraacetic acid

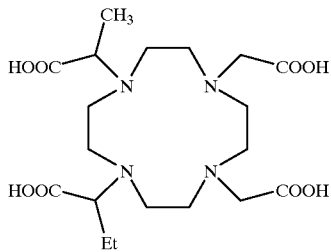

α1-Methyl-α4-ethyl-1,4,7,10-tetraazacyclododecane-1,4,7-triacetic acid, prepared according to the procedure described in example 14B, is reacted with bromoacetic acid, according to the procedure described in example 3, to obtain the desired product.

The $^1$H-NMR, $^{13}$C-NMR, IR and MS spectra are consistent with the indicated structure.

EXAMPLE 17

Synthesis of 11-oxo-1,4,7,10-tetradecane-4,7-diacetic acid (X)

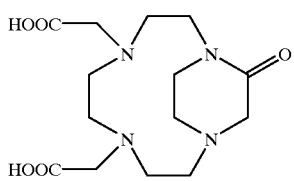

50 g (0.235 mol) of 1,4,7,10-tetraazabicyclo[8.2.2]tetradodecan-2-one, prepared as described in example 1, are dissolved in 500 ml of deionized water. 78 g (0.564 mol) of bromoacetic acid are added, pH is adjusted to 13 by addition of 1N NaOH and the mixture is reacted at room temperature for 12 h, keeping pH at 13 through gradual additions of 1N NaOH. 500 ml of water are added and the resulting solution is percolated on a column containing 2.5 L of cationic exchanger resin Duolite C20MB (Rohm & Haas), washing repeatedly with water, then eluting with 2N ammonia. The useful fractions are concentrated at reduced pressure to a residue, which is redissolved in 300 ml of deionized water. The solution is percolated on a column containing 4 L of resin Amberlite XAD1600, eluting subsequently with deionized water. The fractions containing the pure product are combined and concentrated to dryness at reduced pressure, finally dried in a static drier at 50° C. under vacuum, to obtain 60.2 g (0.183 mol) of the desired product.

Yield: 78%

The $^1$H-NMR, $^{13}$C-NMR, IR and MS spectra are consistent with the indicated structure.

EXAMPLE 18

Synthesis of 1,4,7,10-tetraazacyclododecane-1,4,7-triacetic acid (DO3A) sodium salt

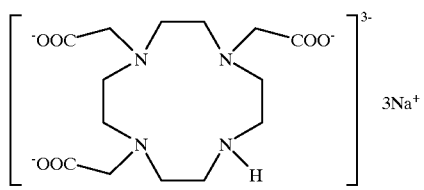

50 g (0.152 mol) of 11-oxo-1,4,7,10-tetraazacyclododecane-4,7-diacetic acid, prepared as described in example 8, are dissolved in 240 g of 10% NaOH. The solution is refluxed overnight, then cooled and pH is adjusted to 12 by addition of conc. HCl. The resulting solution contains 52,6 g (0.152 mol) of 1,4,7,10-tetraazacyclododecane-1,4,7-triacetic acid, as trisodium salt, which can directly be used for the synthesis of tetraacetic acid ligands differentiated at the 1-position.

EXAMPLE 19

Preparation of Gadoteridol

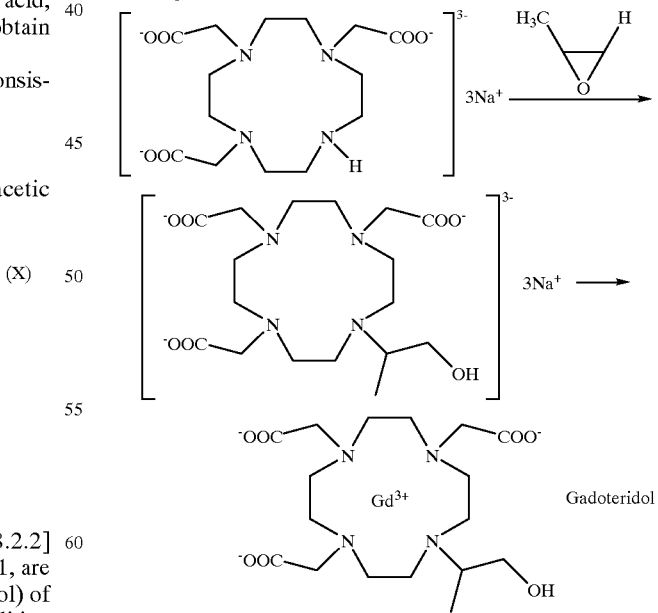

The solution of 1,4,7,10-tetraazacyclododecane-1,4,7-triacetic acid sodium salt is directly reacted, as described in EP 292689, with propylene oxide to give the alkylated product, which can easily be complexed with gadolinium to give the final Gadoteridol.

EXAMPLE 20

Preparation of Gadobutrol

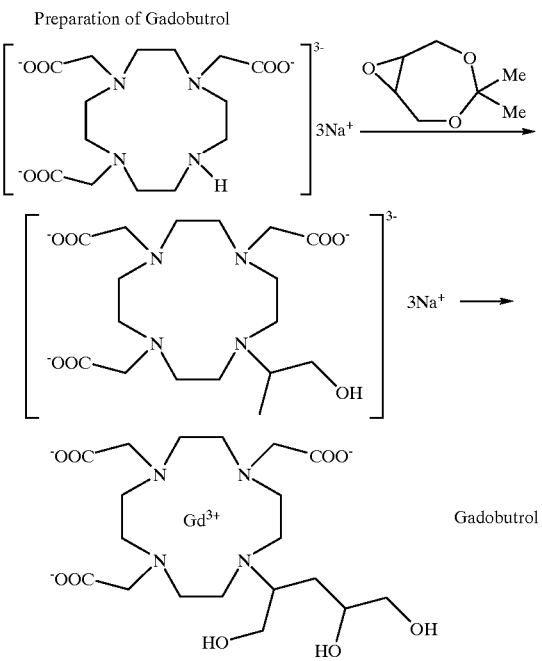

The solution of 1,4,7,10-tetraazacyclododecane-1,4,7-triacetic acid sodium salt is directly reacted, as described in EP 448191, with 4,4-dimethyl-3,5,8-trioxabicyclo[5.1.0]octane to give the alkylated product, which can, easily be complexed with gadolinium to give the final Gadobutrol.

EXAMPLE 21

Synthesis of 1,4,7,10-tetraazacyclododecane-1,4,7-triacetic acid (DO3A)

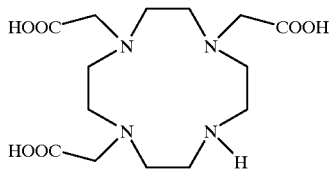

50 g (0.235 mol) of 1,4,7,10-tetraazabicyclo[8.2.2]tetradodecan-2-one, prepared as described in example 1, are dissolved in 500 ml of deionized water. 78 g (0.5646 mol) of bromoacetic acid are added, pH is adjusted to 13 by addition of 1N NaOH and the mixture is reacted at room temperature for 12 h, keeping pH at 13 through gradual additions of 1N NaOH. pH is adjusted to 14 with NaOH in pellets and the solution is refluxed overnight, then diluted with 500 ml of deionized water and percolated on a column containing 3 L of cationic exchanger resin Duolite C20MB (Rohm & Haas). The column is repeatedly washed with water, then eluted with 2N ammonia. The fractions containing the product are combined and concentrated at reduced pressure to a residue, which is redissolved in 300 ml of water. The solution is acidified with sulfuric acid to pH 2, cooled and gradually added with acetone (600 mL). After 3 h crystallization, the solid is filtered, washed with a water/acetone=1:2 mixture, then dried in a static drier at 50° C. under vacuum to obtain 78 g (0.176 mol) of DO3A, salified as sulfate.

Yield: 75%

The $^1$H-NMR, $^{13}$C-NMR, IR and MS spectra are consistent with the indicated structure.

EXAMPLE 22

Synthesis of α4,α7-bis[(phenylmethoxy)methyl]-1,4,7,10-tetraazacyclododecane-1,4,7,10-tetraacetic acid

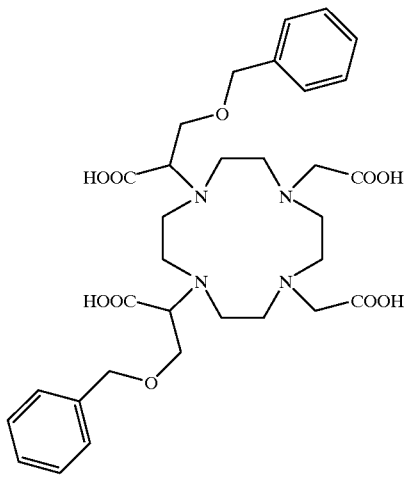

A) α1,α4-bis[(Phenylmethoxy)methyl]-1,4,7,10-tetraazacyclododecane-1,4,7-triacetic acid

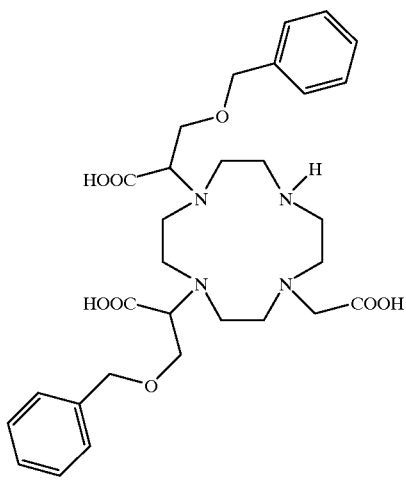

1,4,7,10-tetraazabicyclo[8.2.2]tetradodecan-2-one is reacted with 2-bromo-3-(phenylmethoxy)propanoic acid methyl ester or with 2-trifluoromethanesulfonate-3-(phenylmethoxy)propanoic acid methyl ester in DMF, in the presence of triethylamine. The ester is hydrolysed while opening the lactam, to obtain the desired product.

The $^1$H-NMR, $^{13}$C-NMR, IR and MS spectra are consistent with the indicated structure.

B) α1,α4-bis[(Phenylmethoxy)methyl]-1,4,7,10-tetraazacyclododecane-1,4,7,10-tetraacetic acid α4,α7- bis[(phenylmethoxy)methyl]-1,4,7,10-tetraazacyclododecane- 1,4,7-triacetic acid prepared in the above step is reacted with bromoacetic acid, according to the procedure described in example 3, to obtain the desired product.

The $^1$H-NMR, $^{13}$C-NMR, IR and MS spectra are consistent with the indicated structure.

EXAMPLE 23

Synthesis of α1,α4-bis(hydroxymethyl)-1,4,7,10-tetraazacyclododecane-1,4,7,10-tetraacetic acid

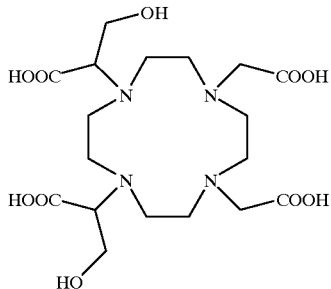

The product described in example 22 is subjected to catalytic hydrogenation, according to the procedure described in example 6, to obtain the desired product.

The $^1$H-NMR, $^{13}$C-NMR, IR and MS spectra are consistent with the indicated structure.

EXAMPLE 24

Synthesis of 1,4,7,10-tetraazabicyclo[8.2.2]-tetradodecan-2-one (III) with piperazine in different pH, temperature and stoichiometry conditions.

The procedure described in example 2 is followed, in the conditions reported in the following table:

| mol piperazine/mol (I) | pH | T (° C.) | t (h) | % Yield |
|---|---|---|---|---|
| 2 | 5 | 100 | 48 | 35 |
| 2 | 6 | 100 | 48 | 48 |
| 2 | 7 | 100 | 48 | 45 |
| 4 | 6.5 | 100 | 24 | 55 |
| 6 | 6 | 80 | 48 | 62 |
| 6 | 9 | 100 | 24 | 52 |
| 7 | 7 | 80 | 48 | 55 |
| 7 | 8 | 100 | 12 | 40 |
| 8 | 8.5 | 100 | 48 | 48 |
| 8 | 9 | 100 | 24 | 42 |
| 10 | 7 | 100 | 18 | 56 |
| 10 | 6 | 100 | 12 | 65 |
| 30 | 5 | 100 | 24 | 55 |

EXAMPLE 25

Synthesis of 1,4,7,10-tetraazabicyclo[8.2.2]-tetradodecan-2-one (I) with piperazine, without recovery of piperazine.H$_3$PO$_4$ 50 g (0.254 mol) of 2α,4α,6α,8α-decahydrotetraazacyclopent[fg]acenaphthylene, prepared as described in MI96A001257, are dissolved in 500 ml of water. 173 g (2 mol) of piperazine are added thereto and pH is adjusted to 6 with conc. HCl (about 286 g). The solution is refluxed for 24 h, then cooled to room temperature, alkalinized to pH 12 with NaOH and concentrated to small volume in rotary evaporator at residual pressure. Methanol is added and the inorganic salts are filtered off. The filtrate is concentrated to dryness at reduced pressure, then repeatedly extracted with hot toluene, and insolubles are filtered off. The toluene extracts are combined, concentrated and cooled. After crystallization at 5° C. overnight, the residue is filtered and recrystallized from toluene, then dried in a static drier at 50° C. under vacuum, to obtain 145 g of piperazine.

Recovery yield: 83%

The toluene mother liquors are further concentrated to small volume, then left to crystallize at 5° C. for 24 h, filtered and recrystallized from toluene, to obtain 31 g of (III).

Yield: 57%

The $^1$H-NMR, $^{13}$C-NMR, IR and MS spectra are consistent with the indicated structure.

What is claimed is:

1. A process for the preparation of the compounds of formula (VII) starting from compound (I), through the monoalkylation reaction of the compound (I) with the alkylating agent (VI), to give the intermediate compound of formula (IX) and the subsequent hydrolysis of the compound (IX), to give the intermediate compound of formula (X), which is alkylated again with the alkylating agent (VI), to give the compounds of formula (VII), as represented in the following Scheme:

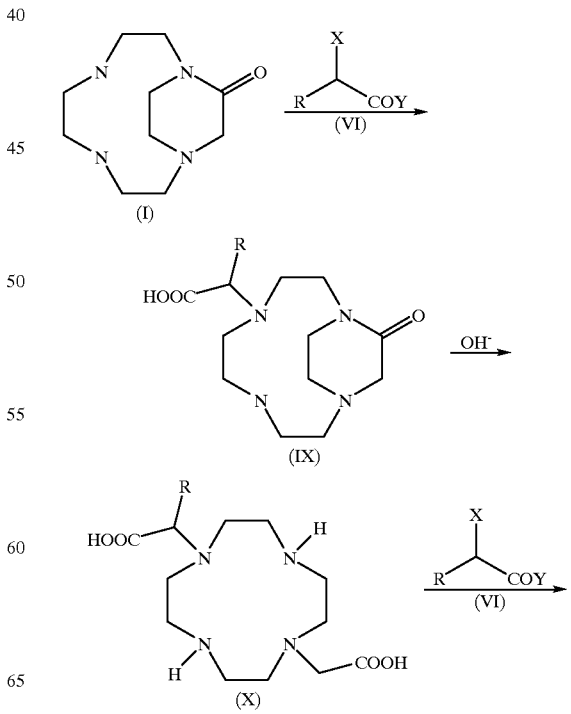

-continued

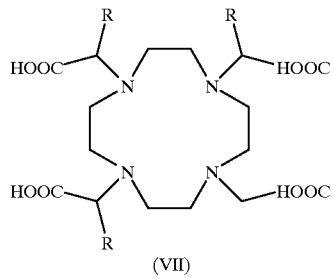

in which
R is a hydrogen atom, a straight, branched or cyclic $C_1$–$C_6$ alkyl group, unsubstituted or substituted with 1 to 10 oxygen atoms, or a $C_1$–$C_{20}$ alkyl group, optionally interrupted by a phenylene, phenyloxy or phenylenedioxy, in its turn substituted with a straight or branched $C_1$–$C_6$ alkyl group, unsubstituted or substituted with 1 to 7 hydroxy groups or with 1 to 3 $C_1$–$C_7$ groups;
the aromatic group can be unsubstituted or substituted with alkoxy groups or halogens, carboxy, carbamoyl, alkoxycarbonyl, sulfamoyl, hydroxyalkyl, amino, acylamino, acyl, hydroxyacyl groups;
X is a halogen or a sulfonic acid reactive residue;
Y is a —OH or —OR, group, wherein $R_1$ is a straight or branched $C_1$–$C_4$ alkyl group; and
when Y is the same as —$OR_1$.

2. A process for the preparation of the compounds of formula (XII), in which compound (X), obtainable according to the process of claim 1, is alkylated with the alkylating agent (XI) as represented in the following Scheme:

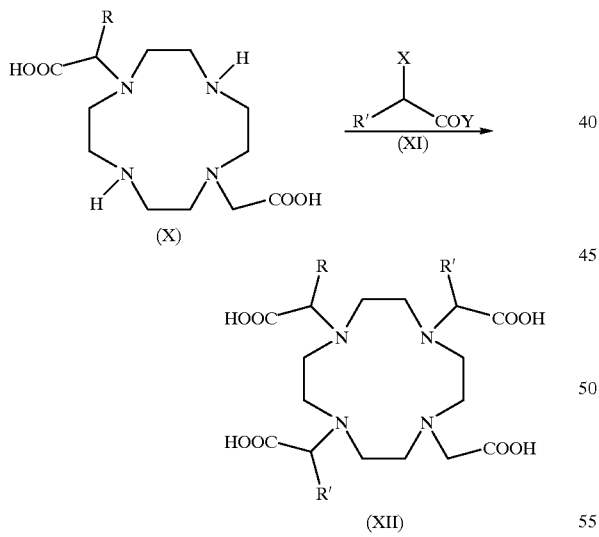

in which R', independently of R, has the same meanings as R defined in claim 1.

3. A process as claimed in claim 2, for the preparation of α1,α7-bis[(phenylmethoxy)methyl]-α4-methyl-1,4,7,10-tetraazacyclododecane-1,4,7,10-tetraacetic acid.

4. A process as claimed in claim 1, for the preparation of 1,4,7,10-tetraazacyclododecane-1,7-diacetic acid (1,7-DO2A) by alkylation of compound (I) with the alkylating agent (VIII) through the formation of the intermediate 12-oxo-1,4,7,10-tetraazabicyclo[8.2.2]tetradecane-4-acetic acid (XIII), which by basic hydrolysis gives 1,7-DO2A.

5. A process as claimed in claim 1, for the preparation of 1,4,7,10-tetraazacyclododecane-1,4,7,10-tetraacetic acid (DOTA), in which the alkylating agent (VI) corresponds to the alkylating agent (VIII) and the alkylation reaction is carried out in aqueous solution at pH 10–12 and at temperatures from 25 to 50° C.

6. A process as claimed in claim 1, for the preparation of compounds of formula (XIV), in which the alkylating agent (VI) corresponds to the alkylating agent (VIIIa) in the first alkylation step, as represented in the following Scheme:

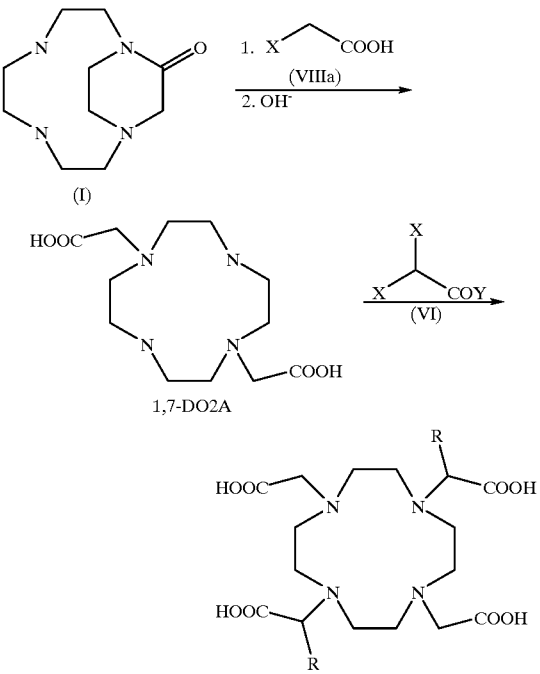

in which R, X and Y have the meanings defined above in claim 1.

7. A process as claimed in claim 6, for the preparation of α1,α7-bis[(phenylmethoxy)methyl]-1,4,7,10-tetraazacyclododecane-1,4,7,10-tetraacetic acid.

* * * * *